(12) United States Patent
Berggren

(10) Patent No.: US 9,462,973 B2
(45) Date of Patent: Oct. 11, 2016

(54) METHODS FOR MONITORING PHYSIOLOGICAL STATUS OF A BODY ORGAN

(71) Applicant: BioCrine AB, Stockholm (SE)

(72) Inventor: Per-Olof Berggren, Solna (SE)

(73) Assignee: BioCrine AB, Stockholm (SE)

( * ) Notice: Subject to any disclaimer, the term of this patent is extended or adjusted under 35 U.S.C. 154(b) by 402 days.

(21) Appl. No.: 13/950,710

(22) Filed: Jul. 25, 2013

(65) Prior Publication Data

US 2014/0033332 A1    Jan. 30, 2014

Related U.S. Application Data

(60) Provisional application No. 61/676,578, filed on Jul. 27, 2012.

(51) Int. Cl.
*A61K 48/00* (2006.01)
*A61B 5/00* (2006.01)
*A61B 3/10* (2006.01)
*A61K 49/00* (2006.01)

(52) U.S. Cl.
CPC ............... *A61B 5/425* (2013.01); *A61B 3/10* (2013.01); *A61B 5/0068* (2013.01); *A61B 5/0071* (2013.01); *A61B 5/4227* (2013.01); *A61B 5/4842* (2013.01); *A61B 5/4848* (2013.01); *A61K 49/0008* (2013.01)

(58) Field of Classification Search
CPC ............................. A61B 5/425; A61B 5/4227
See application file for complete search history.

(56) References Cited

U.S. PATENT DOCUMENTS

| 8,030,288 B2 | 10/2011 | Berggren |
| 8,084,439 B2 | 12/2011 | Berggren |
| 8,507,444 B2 | 8/2013 | Berggren |
| 8,716,241 B2 | 5/2014 | Berggren |
| 2009/0060843 A1 | 3/2009 | Berggren |
| 2011/0244509 A1 | 10/2011 | Berggren |

FOREIGN PATENT DOCUMENTS

WO    2009/027106    3/2009

OTHER PUBLICATIONS

Perez et al. Diabetologia 54(5):1121-1126, May 2011, printout contains pp. 1-13.*
International Search Report for PCT/EP2013/65781, mailed Sep. 3, 2013.
Adeghate E, Donath T (1990) Morphological findings in long-term pancreatic tissue transplants in the anterior eye chamber of rats. Pancreas 5:298-305.
Adeghate, et al. (2000) "Morphological changes in pancreatic tissue transplants in rats," Transplantation Proceedings, 32(7): 2478.
Alanentalo, T. et al. High-resolution three-dimensional imaging of islet-infiltrate interactions based on optical projection tomography assessments of the intact adult mouse pancreas. J Biomed Opt 13, 054070 (2008).
Bock, T., Pakkenberg, B. & Buschard, K. Increased islet volume but unchanged islet number in ob/ob mice. Diabetes 52, 1716-1722 (2003).
Butler PC, Meier JJ, Butler AE, Bhushan A (2007) The replication of beta cells in normal physiology, in disease and for therapy. Nat Clin Pract Endocrinol Metab 3:758-768.
Chen, H. et al. PDGF signalling controls age-dependent proliferation in pancreatic β-cells. Nature 478,349-355 (2011).
Cao R, Brakenhielm E, Wahlestedt C, Thyberg J, Cao Y (2001) Leptin induces vascular permeability and synergistically stimulates angiogenesis with FGF-2 and VEGF. Proc Natl Acad Sci U S A 98:6390-6395.
Ellett, J., Evans, Z., Zhang, G., Chavin, K. & Spyropoulos, D. A rapid PCR-based method for the identification of ob mutant mice. Obesity (Silver Spring) 17,402-404 (2009).
Giordano, E. et al. B-cell size influences glucose-stimulated insulin secretion. Am J Physiol 265, C358-64 (1993).
Hanley, S. C. et al. {beta}-Cell mass dynamics and islet cell plasticity in human type 2 diabetes. Endocrinology 151, 1462-1472 (2010).
Greene, et al. (1952) "The significance of the heterologous transplantability of human cancer," Cancer, 5(1):24-44.
Hellerström C, Hellman B (1961) The blood circulation in the islets of Langerhans visualized by the fluorescent dye vasoflavine. Studies in normal and obese-hyperglycemic mice. Acta Soc Med Ups 66:88-94.
Ingalls AM, Dickie MM, Snell GD (1950) Obese, a new mutation in the house mouse. J Hered. 41:317-318.
Khan, A. et al. Long-term leptin treatment of ob/ob mice improves glucose-induced insulin secretion. Int J Obes Relat Metab Disord 25,816-821 (2001).
Kim A et al. (2009) Islet architecture: A comparative study. Islets 1:129-136.
Lindstrom P (2007) The physiology of obese-hyperglycemic mice [ob/ob mice]. Scientific-WorldJournal 7:666-685.
Lamprianou, S. et al. High-resolution magnetic resonance imaging quantitatively detects individual pancreatic islets. Diabetes 60, 2853-2860 (2011).
Lee, J.-W. & Romsos, D. R. Leptin administration normalizes insulin secretion from islets of Lep(ob)/Lep(ob) mice by food intake-dependent and -independent mechanisms. Exp Biol Med (Maywood) 228,183-187 (2003).
Lindström, P. β-Cell Function in Obese-Hyperglycemic Mice [ob/ob Mice]. The Islets of Langerhans 654, 463-477 (2010).

(Continued)

*Primary Examiner* — Marcia S Noble

(74) *Attorney, Agent, or Firm* — McDonnell Boehnen Hulbert & Berghoff LLP

(57) ABSTRACT

The present invention provides method for monitoring physiological status of an organ in a subject by monitoring morphological changes over time in transplanted tissue on an eye of the subject.

14 Claims, 5 Drawing Sheets

(56) References Cited

OTHER PUBLICATIONS

Lee, Y. C. & Nielsen, J. H. Regulation of beta cell replication. Mol. Cell. Endocrinol. 297, 18-27 (2009).

Mallette, et al. (1996) "Growth in culture of trypsin dissociated thyroid cells from adult rats," Experimental Cell Research, 41(3): 642-651.

Menger MD, Vajkoczy P, Leiderer R, Jäger S, Messmer K (1992) Influence of experimental hyperglycemia on microvascular blood perfusion of pancreatic islet isografts. J Clin Invest 90:1361-1369.

Morioka, T. et al. Disruption of leptin receptor expression in the pancreas directly affects beta cell growth and function in mice. J Clin Invest 117, 2860-2868 (2007).

Nir, T., Melton, D. A. & Dor, Y. Recovery from diabetes in mice by beta cell regeneration. J Clin Invest 117,2553-2561 (2007).

Nyman, L., Ford, E., Powers, A. & Piston, D. Glucose-dependent blood flow dynamics in murine pancreatic islets in vivo. Am J Physiol Endocrinol Metab 298, E807-14 (2010).

Ogilvie, R. F. The islands of langerhans in 19 cases of obesity. J. Phathol. Bacteriol. 37, 473-481 (1933).

Parsons, J. A., Bartke, A. & Sorenson, R. L. Number and size of islets of Langerhans in pregnant, human growth hormone-expressing transgenic, and pituitary dwarf mice: effect of lactogenic hormones. Endocrinology 136, 2013-2021 (1995).

Park, S.-Y. & Bell, G. I. Noninvasive monitoring of changes in pancreatic beta-cell mass by bioluminescent imaging in MIP-luc transgenic mice. Horm Metab Res 41, 1-4 (2009).

Park S, Hong SM, Sung SR, Jung HK (2008) Long-term effects of central leptin and resistin on body weight, insulin resistance, and beta-cell function and mass by the modulation of hypothalamic leptin and insulin signaling. Endocrinology 149:445-454.

Rieck, S. & Kaestner, K. H. Expansion of beta-cell mass in response to pregnancy. Trends Endocrinol. Metab. 21, 151-158 (2010).

Speier, S. et al. Noninvasive in vivo imaging of pancreatic islet cell biology. Nat Med 14, 574-578 (2008).

Greene, et al. (1957), "Heterotransplantation of Tumors," Annals of the New York Academy of Sciences, 69(4): 818-829.

Seufert, J. Leptin effects on pancreatic beta-cell gene expression and function. Diabetes 53 Suppl 1, S152-8 (2004).

Singhal, T. et al. Pancreatic beta cell mass PET imaging and quantification with [11C]DTBZ and [18F]FP-(+)-DTBZ in rodent models of diabetes. Mol Imaging Biol 13, 973-984 (2011).

Starich GH, Zafirova M, Jablenska R, Petkov P, Lardinois CK (1991) A morphological and immunohistochemical investigation of endocrine pancreata from obese ob+/ob+ mice. Acta Histochem 90:93-101.

Speier S et al. (2008) Noninvasive high-resolution in vivo imaging of cell biology in the anterior chamber of the mouse eye. Nature Protocols 3:1278-1286.

Seufert J, Kieffer TJ, Habener JF (1999) Leptin inhibits insulin gene transcription and reverses hyperinsulinemia in leptin-deficient ob/ob mice. Proc Natl Acad Sci U S A 96:674-679.

Tassava, T., Okuda, T. & Romsos, D. Insulin secretion from ob/ob mouse pancreatic islets: effects of neurotransmitters. Am J Physiol 262, E338-43 (1992).

Villiger, M. et al. In vivo imaging of murine endocrine islets of Langerhans with extended-focus optical coherence microscopy. Diabetologia 52, 1599-1607 (2009).

Virostko, J. et al. Multimodal image coregistration and inducible selective cell ablation to evaluate imaging ligands. Proceedings of the National Academy of Sciences 108,20719-20724 (2011).

Westman, S. Development of the obese-hyperglycaemic syndrome in mice. Diabetologia 4, 141-149 (1968).

Wrenshall GA, Andrus SB, Mayer J, Jones AK, Dolan P (1955) High levels of pancreatic insulin coexistent with hyperplasia and degranulation of beta cells in mice with the hereditary obese-hyperglycemic syndrome. Endocrinology 56:335-340.

Zhang, Y. et al. Positional cloning of the mouse obese gene and its human homologue. Nature 372, 425-432 (1994).

\* cited by examiner

METHODS FOR MONITORING PHYSIOLOGICAL STATUS OF A BODY ORGAN

CROSS REFERENCE

This application claims priority to U.S. Provisional Patent Application Ser. No. 61/676578, filed Jul. 27, 2012, incorporated by reference herein in its entirety.

BACKGROUND

A number of different experimental approaches allow for the quantification of beta cell mass and for eventually displaying the remodeling of islets. In vitro techniques include the analysis of histological sections of pancreas by point counting morphometry and the direct measurements of islet dimensions in dissected pancreatic tissue. Ex vivo imaging techniques comprise the imaging of exteriorized pancreas by confocal microscopy or optical coherence microscopy. Finally, several non-invasive in vivo imaging techniques aim at the longitudinal quantification of total beta cell mass, i.e. magnetic resonance imaging (MRI), positron emission tomography (PET), bioluminescence imaging, or combined multimodal imaging. However, these techniques only provide indirect evidence for islet plasticity, as these various techniques do not offer the possibility to follow morphological changes in individual islets over time.

SUMMARY OF THE INVENTION

The present invention provides methods for monitoring physiological status of an organ in a subject, comprising monitoring morphological changes over time in transplanted tissue on an eye of the subject, wherein the tissue is from an organ of interest, and wherein the morphological changes over time in the transplanted tissue on the eye of the subject indicates a physiological status of the organ of interest in the subject. In one embodiment, the method is used to monitor efficacy of a course of treatment for a disorder in the subject. In this embodiment, the course of treatment may comprise administration of a therapeutic to the subject, and wherein the method monitors efficacy of the therapeutic in the individual. In a further embodiment, the course of treatment may comprise a diet and/or an exercise regimen, and the method monitors efficacy of the diet and/or exercise regimen in the individual.

In another embodiment the transplanted tissue may be obtained from the subject. In a further embodiment, the organ of interest may selected from the group consisting of pancreas, lung, heart, brain, kidney, liver, small intestine, large intestine, colon, stomach, gall bladder, esophagus, ureter, urethra, ovary, uterus, breast, spinal cord, prostate, hypothalamus, adrenal gland, pituitary gland, thyroid gland, parathryroid gland, pineal gland, spleen, thymus, rectum, mammary gland, seminal vesicles, glomeruli, fat tissue, tumor, and testes.

In another embodiment, the organ of interest may comprise an exocrine gland, including but not limited to sweat glands, salivary glands, mammary glands, stomach, liver, and pancreas. In another embodiment, the organ of interest may comprise an endocrine gland, including but not limited to a pituitary gland, pancreas, ovaries, testes, thyroid gland, and adrenal gland. In one embodiment, the organ of interest is the pancreas. In this embodiment, the tissue may comprise isolated pancreatic islets of Langerhans.

In various embodiments, the morphological changes may be selected from the group consisting of cell size in the tissue, cell volume in the tissue, cell area in the tissue, cell shape in the tissue, cell death in the tissue, cell proliferation in the tissue, cell mass in the tissue, blood perfusion in the tissue, optical reflectivity of cells in the tissue, and granulation of cells in the tissue. In another embodiment, the morphological changes may be monitored by microscopy. In a further embodiment, the subject is a non-human mammal In one embodiment, the non-human mammal has an animal model of a human disease. In another embodiment, the subject is a human, wherein the human has a disease relating to the organ of interest. In various embodiments, the disease may comprise diabetes and the organ of interest may be the pancreas, or the disease may comprise cancer and the organ of interest thus comprises a tumor. In a further embodiment, the methods may further comprise administering a therapeutic or test compound to the subject, and monitoring morphological changes resulting from the administering.

DETAILED DESCRIPTION OF THE INVENTION

Figure 1:
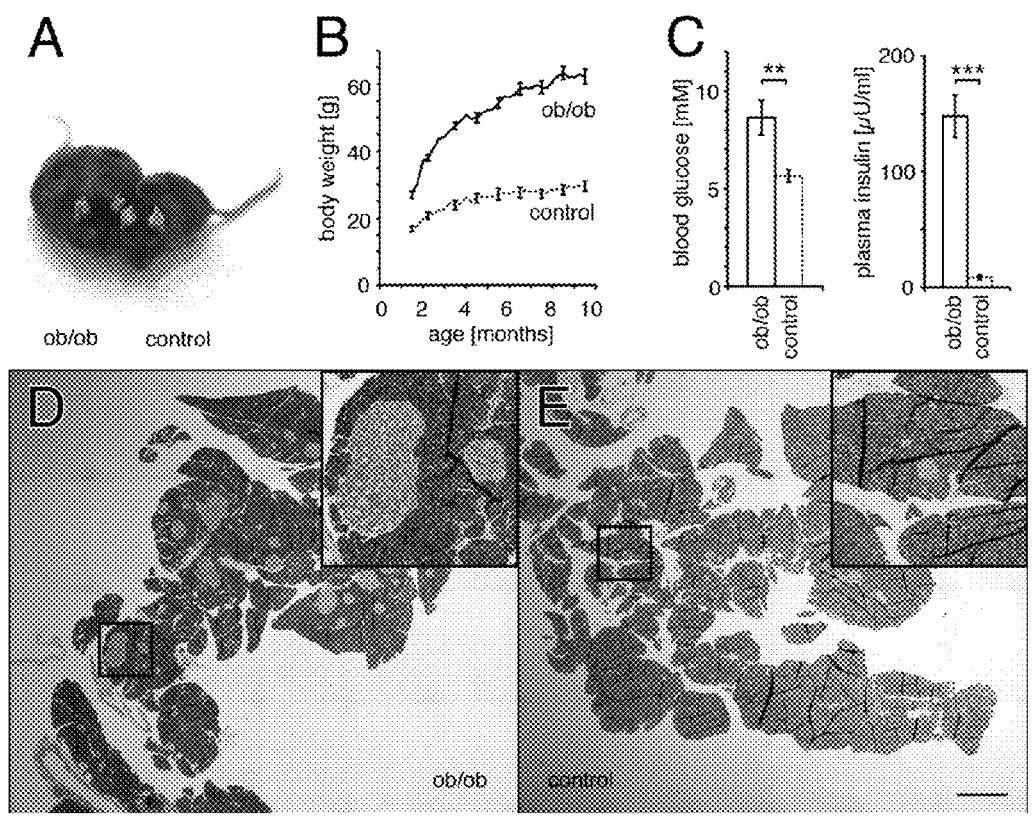
FIG. 1. Increased islet size to adapt to high insulin demandin the ob/ob mouse pancreas. (A) representative morphological appearance of the ob/ob mouse (left) compared to a control littermate (right), showing a strong obese phenotype; (B) fasted body weight of ob/ob and control mice at different ages shows a rapid increase in body mass in the ob/ob mice; (C) fasted blood glucose and plasma insulin levels in ob/ob and control mice; (D) image montage of 5 µm-thick sections of ob/ob and (E) control littermate pancreata, stained by hematoxylin and eosin. Note the staining of islet sections in light grey; insets in (D, E) show a magnified view of typical islet dimensions and morphology. Mice were (A) 4 months, (C) 3 months, and (D, E) 8 months of age. (B, C): values for mixed males and females (n=5 males+4 females, and 5 males+5 males for ob/ob and control littermates, respectively). Scale=1 mm, inset dimension represents 1 mm×1 mm. Values are average±s.e.m.; $p<0.01$; *$p<0.001$.

All references cited are herein incorporated by reference in their entirety. Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, Calif.), *Culture of Animal Cells: A Manual of Basic Technique*, 2$^{nd}$ Ed. (R. I. Freshney. 1987. Liss, Inc. New York, N.Y.), *Gene Transfer and Expression Protocols*, pp. 109-128, ed. E. J. Murray, The Humana Press Inc., Clifton, N.J.), and the Ambion 1998 Catalog (Ambion, Austin, Tex.).

As used herein, the singular forms "a", "an" and "the" include plural referents unless the context clearly dictates otherwise. "And" as used herein is interchangeably used with "or" unless expressly stated otherwise.

All embodiments of any aspect of the invention can be used in combination, unless the context clearly dictates otherwise.

In a first aspect, the present invention provides methods for monitoring physiological status of an organ in a subject, comprising monitoring morphological changes over time in transplanted tissue on an eye of the subject, wherein the tissue is from an organ of interest, and wherein the morphological changes over time in the transplanted tissue on the eye of the subject indicates a physiological status of the organ of interest in the subject.

As shown in the examples that follow, the inventors have demonstrated a novel methodology based on the use of a few "reporter islets" transplanted into the anterior chamber of the eye, serving as in vivo indicators of morphological changes occurring in situ in the pancreatic islet population over a course of several months. This concept is illustrated in the examples by the longitudinal visualization and quantification of obesity-induced islet growth and vascularization patterns that were subsequently normalized after drug treatment, showing for the first time evidence for individual islet remodeling by the expansion or reduction of its insulin-secretory potential in adaptation to specific needs. Hence "reporter islets" serve as optically accessible indicators of islet function in the pancreas, and can be used as personalized in vivo biological markers serving as efficient readouts for both diagnosing islet malfunction and monitoring the effects of specific treatments on the regulation of islet cell mass and functional status.

The subject can be any subject of interest, preferably a mammal, including but not limited to mice, rats, rabbits, dogs, cats, primates, chimps, baboons, and humans.

While the methods are exemplified by use of reporter islets as to assess pancreatic physiological status, it will be understood by those of skill in the art, based on the teachings herein, that the methods can be applied to a wide range of organ types by use of transplanted tissues from the organ of interest. The physiologic status of any suitable organ of interest can be assessed by the methods of the invention. In one embodiment, the organ of interest is selected from the group consisting of pancreas, lung, heart, brain, kidney, liver, small intestine, large intestine, colon, stomach, gall bladder, esophagus, ureter, urethra, ovary, uterus, breast, spinal cord, prostate, hypothalamus, adrenal gland, pituitary gland, thyroid gland, parathryroid gland, pineal gland, spleen, thymus, rectum, sweat glands, salivary glands, mammary gland, seminal vesicles, glomeruli, tumor, fat tissue, and testes.

In another embodiment, the organ of interest comprises an exocrine gland. In this embodiment, non-limiting examples of exocrine glands include sweat glands, salivary glands, mammary glands, stomach, liver, and pancreas. In a further embodiment, the organ of interest comprises an endocrine gland. In this embodiment, non-limiting examples of endocrine glands include pituitary gland, pancreas, ovaries, testes, thyroid gland, and adrenal gland.

The transplanted tissue may comprise individual cells, a plurality of cells of the same type, or a plurality of different cell types, such as tissues/tissue portions. The transplanted tissue may be obtained from any suitable source. In one preferred embodiment, the transplanted tissue is obtained from the subject prior to transplantation in the eye. Methods for obtaining small amounts of tissue from organs of interest are well known to those of skill in the art.

Any suitable amount of tissue may be transplanted that minimizes any negative impact of the transplant on vision or other eye function in the subject. As exemplified in the data shown herein, 10-20 islets were transplanted into the anterior chamber of the mouse eye. Based on the teachings herein, those of skill in the art can determine an appropriate amount of tissue to be transplanted for a given subject.

In one embodiment, monitoring of morphological changes in the transplanted tissue begins approximately one month after transplantation, to permit full vascularization and innervation of the transplanted tissue. In another embodiment, monitoring of morphological changes in the transplanted tissue can begin as soon as desired after transplantation; this embodiment can be used, for example, when full vascularization of the transplanted tissue is not required for a given study (for example, when looking at test compound effects on vascularization and/or innervation). In all embodiments, the monitoring can be carried on as long as desired for a given study. If desired, the transplanted tissue may be removed after completion of treatment or for any other reason.

In one preferred embodiment, the organ of interest is a tumor. In this embodiment, the methods may be used, for example, on a non-human mammalian subject to test candidate compounds or other therapies for anti-tumor efficacy, side effects, etc.

In a further preferred embodiment, the organ of interest is the pancreas. In this embodiment, the tissue may be any suitable pancreatic tissue, including but not limited to isolated pancreatic islets of Langerhans. Islets of Langerhans are composed of several different cell types, including alpha-, beta- and delta-cells. These clusters of cells represent the endocrine pancreas and are of major importance for glucose homeostasis. Insufficient release of insulin from beta-cells in response to elevated blood glucose levels leads to diabetes. The regulation of glucose induced insulin secretion from beta-cells is a complex process, modulated by autocrine, paracrine, hormonal and neuronal factors.

Any morphological changes can be assessed as suitable for a given study, and depend at least in part on the type of transplanted tissue and the organ of interest. In non-limiting embodiments, the morphological changes include, but are not limited to cell size in the tissue, cell volume in the tissue, cell area in the tissue, cell shape in the tissue, cell death in the tissue, cell proliferation in the tissue, cell mass in the tissue, blood perfusion in the tissue, optical reflectivity of cells in the tissue, and granulation of cells in the tissue.

For example, in embodiments where the organ of interest is the pancreas and the transplanted tissue comprises isolated islets of Langerhans, exemplary morphological changes include:

(a) changes in beta cell mass (reflects pancreatic physiologic status);
(b) beta cell destruction (may reflect pancreatic pathology);
(c) beta cell hyperplasia and/or cellular hypertrophy (reflects increased insulin content)
(d) beta cell proliferation (reflects pancreatic physiologic status);
(e) islet dimensions (reflects pancreatic physiologic status);
(f) islet damage (may reflect pancreatic pathology);
(g) intra-islet blood vessel diameter (may reflect compensatory mechanism designed to increase microvascular blood perfusion under hyperglycemic conditions);
(h) islet degranulation (reflects insulin secretion levels); and
(i) islet optical reflectivity (indicative of insulin release).

In one embodiment of any embodiment or combination of embodiments of the invention, the methods may be used to monitor the effect on the organ of interest of a therapeutic or test compound administered to the subject. In one non-limiting example, the methods comprise assessing efficacy of a course of treatment for a disorder in the subject. In one non-limiting embodiment, the subject suffers from diabetes (type 1 or type 2 diabetes), or the subject is an animal model of diabetes and the methods are used to monitor efficacy of a course of treatment that the subject is undergoing to treat the diabetes. In one embodiment, the course of treatment comprises administration of a therapeutic or candidate therapeutic to the subject, and the method monitors efficacy of the therapeutic, side effects of the therapeutic, effects of dosage changes, and/or any other endpoint of interest in the individual. In another embodiment, the course of treatment comprises a diet and/or an exercise regimen, and wherein the method monitors efficacy of the diet and/or exercise regimen in the individual.

As exemplified below, in vivo imaging of transplanted islets provides 3-dimensional morphological information that allows for a precise quantification of various islet parameters at given time points after transplantation. For example, quantification of average islet volumes over time showed significant differences between ob/ob and control subjects starting from 1 month after transplantation, illustrating a dramatic islet growth in the ob/ob subject. This growth proved to be independent of the subject donor genotype, i.e. a similar growth was observed when transplanting control subject islets into ob/ob subject, demonstrating that i) signaling factors originating from the recipient subject dictate morphological changes of transplanted islets, and ii) the transplanted islets reflect morphological behavior of the recipient's in situ pancreatic islets. The studies shown below further demonstrate that this observed plasticity is reflective of the plasticity occurring in situ in islets located in the pancreas, and that in vivo changes in these morphological parameters caused by treatment for the disorder were also found in the transplanted islets.

Thus, the examples demonstrate that "reporter islets" can reveal, in a representative way, the remodeling of the in situ pancreatic islet population, expanding or reducing their insulin-secretory potential. Hence, this technique permits to "merge" the study of individual islets with the study of islet populations, and has the potential to replace multiple cross-sectional experiments with longitudinal studies. We thus propose the in vivo imaging of "reporter" transplanted tissue into the eye as a versatile tool to identify factors leading to morphological changes in the transplant, and thus the organ of interest.

Transplantation into the eye preferably involves transplantation into the anterior chamber of the eye. The anterior chamber of the eye comprises the front portion of the eye, and includes the structure in front of the vitreous humour, as well as the cornea, iris, ciliary body, and lens. Transplantation of the tissue into the anterior chamber of the eye can comprise placement of the cells into any one or more of these anterior eye chamber compartments. In one non-limiting example, tissue transplants are transplanted via injection through the cornea, allowing engraftment of the transplanted islets onto the iris, permitting observation and imaging through the cornea. Islets transplanted into the anterior chamber of the eye engrafted on the iris, became vascularized, retained their cellular composition, and responded to stimulation. Furthermore, they can be monitored by non-invasive laser scanning microscopy (LSM) allowing in vivo imaging of morphological changes. See, for example, published US patent application 20090060843. Employing the anterior chamber of the eye as a transplantation site permits continuous monitoring of morphological changes in the transplanted tissue, and can be used to elucidate effects of modulatory inputs from, for example, the hormonal and neuronal system, as well as from autocrine/paracrine signals of endocrine or vascular cells.

The morphological changes in the transplanted tissue can be monitored by any suitable technique, including but not limited to direct visualization. In a preferred embodiment, the morphological changes are monitored by microscopy. See, for example, published US patent application 20090060843, and the methods disclosed in the examples that follow. In one preferred embodiment, the morphological changes are monitored by confocal microscopy and/or two-photon microscopy, which provide 3-dimensional morphological information.

The methods comprise monitoring morphological changes over time in transplanted tissue on an eye of the subject. In one embodiment, the subject is administered a therapeutic or test compound of interest via any suitable route of administration, and morphological changes in the transplanted tissue are determined at one or more (i.e.: 1, 2, 3, 4, 5, 6, 7, 8, 9, 10, or more) subsequent time points. Any suitable amount of time between measurements of morphological change can be employed, as deemed appropriate in light of the specifics of the methods being carried out.

In another embodiment, the methods further comprise comparing the morphological changes over time in the transplanted tissue to changes in in situ changes occurring over the same time frame as represented in biopsies obtained from the subject. The in situ changes can be assessed by any suitable technique, including but not limited to histochemical analysis of tissue sections as described in the examples that follow.

EXAMPLE

Reporter Islets Reveal the Adaptive Plasticity of In Situ Pancreatic Islets

Abstract

The islets of Langerhans constitute the endocrine pancreas and are responsible for maintenance of blood glucose homeostasis. They are deeply embedded in the exocrine pancreas and therefore their accessibility for functional studies is limited. To understand regulation of function and survival and assess the clinical outcome of individual treatment strategies for diabetes, a monitoring system continuously reporting on the endocrine pancreas is needed. We describe the application of a natural body window that successfully reports on the properties of in situ pancreatic islets. As proof of principle "reporter islets" were transplanted into the anterior chamber of the eye of leptin-deficient mice. The "reporter islets" displayed obesity-induced growth and vascularization patterns that were reversed by leptin treatment. Hence "reporter islets" serve as optically accessible indicators of islet function in the pancreas, and reflect the efficiency of specific treatment regimens regulating islet plasticity in vivo.

Introduction

Normal fluctuations in blood glucose concentration trigger an orchestrated release of hormones from various cells in the endocrine pancreas, the islets of Langerhans. The beta cell produces and secretes insulin, an essential hormone regulating glucose uptake. A decrease in functional beta cell mass leads to impaired glucose homeostasis and diabetes, a devastating disease with epidemic spreading. An adequate regulation of beta cell mass is thus of paramount importance to adapt to various functional demands always ensuring maintenance of a normal blood glucose concentration (1). The major challenge for functional studies of the islets of Langerhans in health and disease is the fact that they are deeply embedded in the exocrine pancreas and therefore have a limited accessibility. Hence, to understand regulation of function and survival and to assess the clinical outcome of individual treatment strategies for diabetes, there is an ultimate need for a monitoring system continuously reporting on the status of the endocrine pancreas in the living organism.

We have developed a technical platform for non-invasive, longitudinal, in vivo imaging at single cell resolution (2, 3). By applying this in vivo imaging technique to the current study, we wanted to test our hypothesis that islets transplanted into the anterior chamber of the eye can report on the functional status of the endogenous endocrine pancreas and that intervention with pathological processes in the islets of Langerhans indeed can be monitored in the eye. For this purpose we took advantage of the obese mutant mouse (ob/ob) as a model system. This mouse was first described in 1950 (4), it displays impressive islet plasticity during its lifetime and has been extensively studied as a model for obesity and insulin resistance. At a very young age these mice are hyperinsulinemic, hyperglycemic and show a higher than average body weight (5). In addition to a distinct obesity coupled to a strong appetite, these mice display a number of impaired functions, such as reduced metabolic rate, impaired thermogenesis, impaired immunity and infertility (6). In 1994, Friedman and coworkers identified the ob gene encoding for the hormone leptin, produced mainly in adipose tissue (7). This gene is mutated in the ob/ob mouse and as a consequence this mouse is incapable of expressing any functional leptin. Under normal conditions leptin has many different physiological roles but one of its most remarkable functions is to regulate appetite. In response to nutrition, leptin is released from adipose tissue and activates leptin receptors in the hypothalamus, leading to suppression of appetite and as a consequence reduced food intake. Additionally, leptin receptors are expressed in beta cells and are involved in an adipo-insular feedback loop inhibiting insulin expression and release after food intake (8, 9). The lack of leptin in the ob/ob mouse thus results in rapid increase in body weight and, in an effort to compensate for the increased demand for insulin, in beta cell hyperplasia (10). As a consequence the islet cell population of the ob/ob mouse is altered, the percentage of beta cells in comparison to other endocrine cells is particularly high and accounts for more than 90% of total islet cells (11). In the ob/ob mouse the absence of a leptin-driven feedback loop both explains the strong insulin release observed from beta cells, resulting in apparent degranulation (10) and the development of insulin resistance.

By applying the ob/ob mouse as a model system, we could demonstrate the versatile and interesting application of optically-accessible "reporter islets" in the anterior chamber of the eye. These reporter islets successfully monitor beta cell plasticity in situ in the endocrine pancreas and also enable the follow up of a specific treatment regimen.

Results

The ob/ob Mouse Displays Abnormal Physiological Properties

The ob/ob mouse can be morphologically differentiated from its control littermate already at the age of 4 weeks, and its increased body mass becomes increasingly noticeable with advancing age (FIGS. 1A, B). Physiological studies revealed increased fasting blood glucose and insulin levels as compared to control littermates (FIG. 1C). This is in accordance with earlier reports (5) and is indicative of excessive food intake and insulin resistance. Paraffin-embedded sections of ob/ob mouse and control mouse pancreata were stained by hematoxylin and eosin to observe differences in islet morphology. Islet dimension was increased in the ob/ob mouse to provide a large potential insulin secretory capacity in an effort to compensate for the increased food intake (FIGS. 1D, E). While looking at pancreas sections provides information regarding the morphological status of islets at specific time points, dynamic changes cannot be appreciated.

Figure 2:
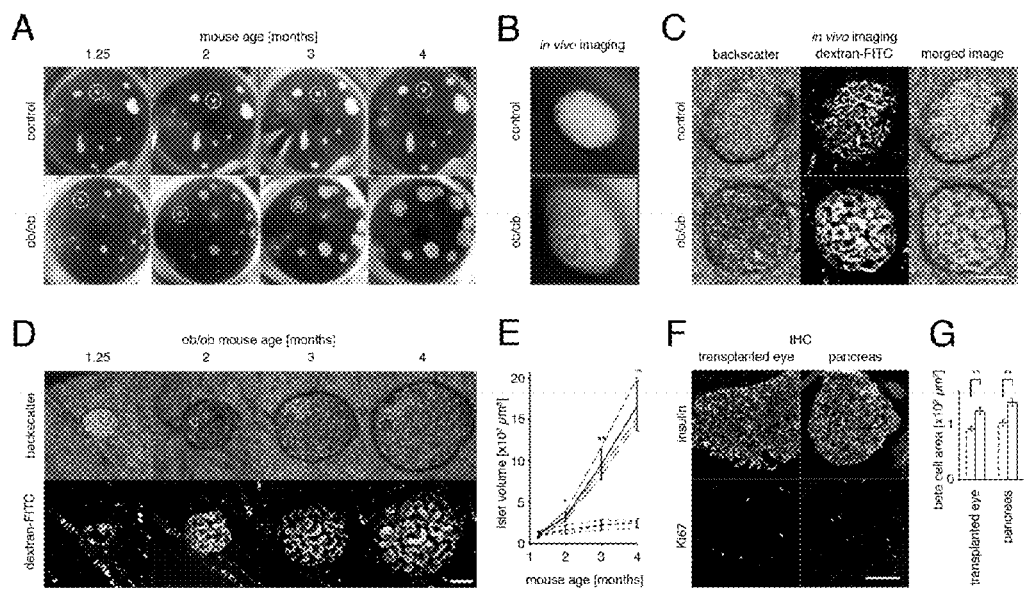
FIG. 2. In vivo longitudinal imaging of islet growth. (A) islets from 4 weeks old mice were transplanted into the anterior chamber of the eye of control (upper lane) and ob/ob (lower lane) mice at 4 weeks of age. Photography of transplanted eyes at different time points shows that individual islets can be identified and followed longitudinally (see yellow dashed circle); (B) magnified views of islet grafts (marked by red frames in A) show the clearly visible large and tortuous blood vessels in the islet engrafted onto the iris of ob/ob recipient; (C) in vivo imaging of single islets 1 month after transplantation by confocal microscopy shows morphological differences between islet grafts in control versus ob/ob mice. Vascularization is imaged by prior intravenous injection of FITC-labeled dextran. Note differences in backscatter intensity and vessel diameters; (D) in vivo imaging of islet grafts at different time points after transplantation by confocal microscopy; (E) quantification of islet volumes by analysis of backscatter images reveals a significantly increased growth in ob/ob (solid lines), as compared to control (dashed lines). Gray lines represent average islet volumes in single mice, black lines represent averaged values obtained per genotype (n=3); (F) immunohistochemistry analysis shows a strong proliferation of beta cells both in ob/ob transplanted eye and pancreas, as seen by insulin and Ki67 staining; (G) average beta cell area was quantified from insulin and DAPI staining, demonstrating that beta cells from ob/ob mice (solid lines) were significantly larger than those from their control littermates (dashed lines). This hypertrophy was similar and independent on whether the islets were located in situ in the pancreas or in the transplanted eye (no significant differences). All images are representative. Confocal images are displayed as maximum intensity projections (MIP) of optical z-stacks. Immunohistochemistry experiments were performed using 4 months old mice (n≥3 per group). Size bars=100 µm. Error bars represent s.e.m.; *p<0.05; **p<0.01.

Intraocular Islet Transplants Mirror the Adaptive Morphological Plasticity of In Situ Endogenous Islets To study the morphological plasticity of these islets over time we therefore transplanted a few "reporter islets" into the anterior chamber of the mouse eye, which can be optically accessed for longitudinal in vivo imaging. Pancreatic islets were isolated from donor mice at the age of 4 weeks and transplanted into the anterior chamber of the eye of age-matched recipients. This in vivo environment contains a rich capillary as well as nervous network that will connect to the engrafted islets and thus permit not only inter-cellular paracrine but also endocrine and nervous input (2, 12). Transplanted islets rapidly engrafted onto the iris and individual islet transplants could be identified repetitively at different time points after transplantation (FIG. 2A). In addition to an increased growth these islets displayed increased intra-islet vessel diameters in the ob/ob recipient (FIG. 2B), as previously documented from dissected pancreatic tissue in vitro (13, 14). The increase in intra-islet vessel diameter could be implicated in a compensatory mechanism designed to increase blood perfusion under hyperglycemic conditions (15). It might also be one approach to optimize endocrine signaling, ensuring that each of the beta cells will have a direct communication with blood flow under this strong proliferative condition. Individual islets were imaged in vivo at different time points in syngeneically transplanted mice by confocal microscopy, and the large and tortuous blood vessels in the ob/ob islet grafts were confirmed by fluorescence imaging (FIG. 2C). Backscatter imaging revealed islet morphology as well as a seemingly degranulated and uneven pattern in the ob/ob mouse islet. The scarce reflection of light is indicative of rapid insulin secretion, which can be explained by disruption of the adipo-insular feedback loop under leptin-deficient conditions (9). Analysis of in situ islets by immunohistochemistry on paraffin-embedded sections showed that islets in the pancreas follow similar distinctive properties between ob/ob and control mice, i.e. CD31 staining showed large vessels in the ob/ob islets and insulin staining was irregular.

The in vivo imaging of transplanted islets by confocal microscopy provides 3-dimensional morphological information that for the first time allows for a precise quantification of islet volume at any given time point after transplantation. Quantification of average islet volumes over time showed significant differences between ob/ob and control mice starting from 1 month after transplantation, illustrating a dramatic islet growth in the ob/ob mouse (FIGS. 2D, E). Interestingly, this growth proved to be independent of the mouse donor genotype, i.e. we observed a similar growth when transplanting control mouse islets into ob/ob mice, demonstrating that in this particular case i) signaling factors originating from the recipient mouse dictate morphological changes of transplanted islets, and ii) the transplanted islets reflect morphological behavior of the recipient's in situ pancreatic islets.

To examine whether this observed plasticity in the anterior chamber of the eye indeed reflects the plasticity occurring in situ in islets located in the pancreas, we compared paraffin-embedded sections of islet transplants and endogenous pancreatic islets by immunohistochemistry. We observed a strong proliferation of beta-cells in the ob/ob mouse islets by staining for insulin and Ki67 (FIG. 2F). This proliferation rate was not significantly different whether measured from in situ pancreatic islets or from islets engrafted in the anterior chamber of the eye (mean±s.e.m.=0.82±0.10%, n=5, and 0.95±0.15%, n=4 mice, respectively). Morphological changes in beta cells were also assessed by immunohistochemistry and revealed an approximately 1.35-fold increase in cell area in the ob/ob mice as compared to control mice, both in in situ islets located in the pancreas and in islet grafts (FIG. 2G). The lack of leptin signaling is a likely contributor to this volume expansion. Indeed it has been shown, using pancreas-specific leptin receptor KO mice, that the disruption of leptin action in islets results in enhanced PI3K/AKT signaling, associated with increases in beta cell size and islet mass (16). Although this compensatory islet growth has been demonstrated in vitro, we have now been able to verify this pattern in the living ob/ob mouse longitudinally by the analysis of single "reporter islets". Importantly, our data are compatible with previous studies where the mean islet volume showed a 4-fold difference between control and ob/ob mice at 2 months of age, either from studies based on isolated islets (17) or from imaging of histological sections spanning the entire pancreas (18).

Figure 3:
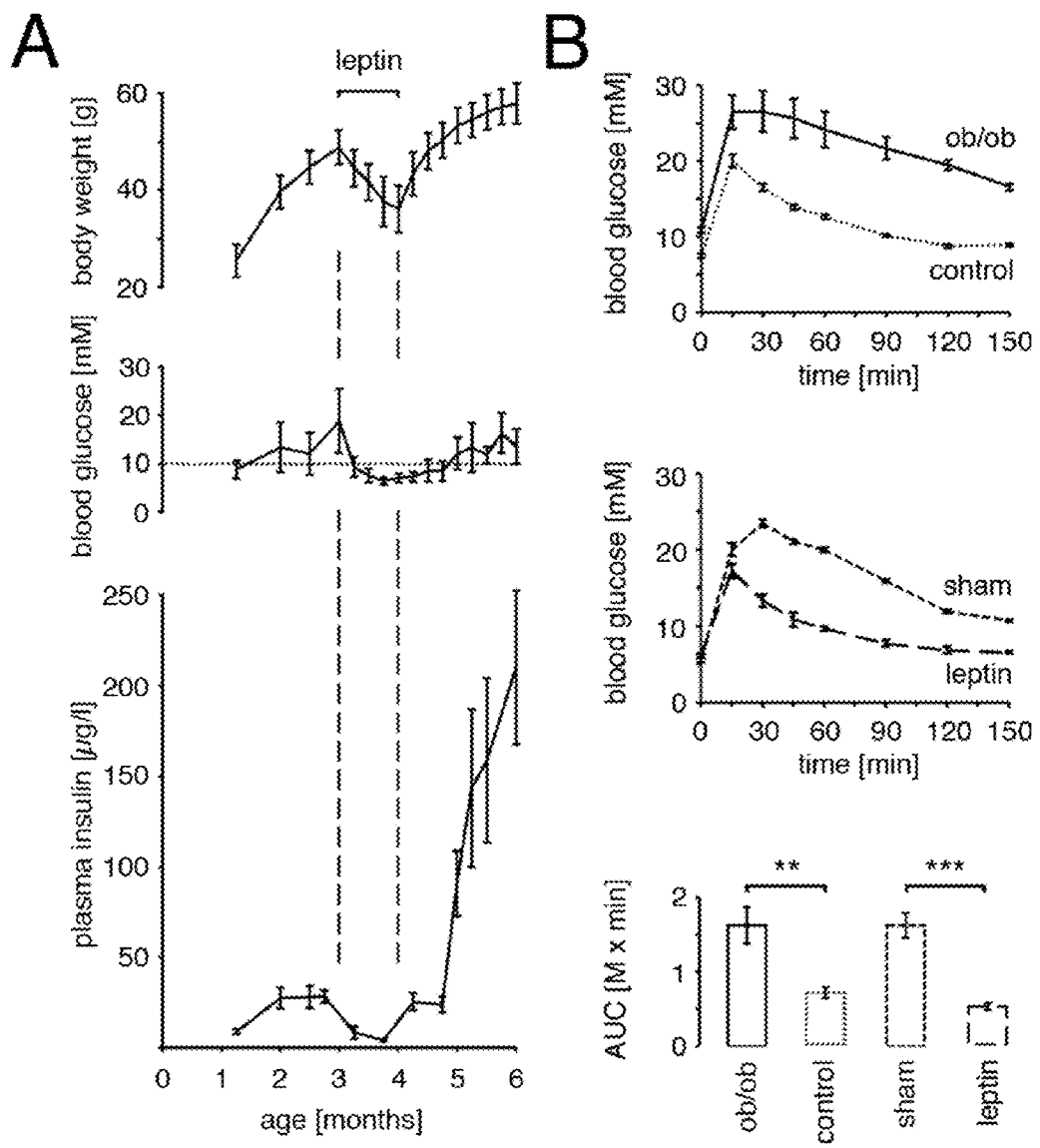
FIG. 3. Physiological effects of leptin treatment on ob/ob mice.(A) ob/ob mice received daily intraperitoneal injections of leptin between 3 and 4 months of age. Body weight, blood glucose and plasma insulin levels were monitored before, during and after the treatment (beginning and end of treatment are represented by vertical dashed lines); (B) intraperitoneal glucose tolerance tests show impaired glucose handling in the ob/ob mouse as compared to control littermate at 4 months of age (top traces), which is normalized by leptin treatment but not by sham treatment (middle traces). The lower bar graph shows area under the curve (AUC) values from the above traces, demonstrating the beneficial effect of leptin on glucose handling. Values are average±s.e.m.; p<0.01; *p<0.001.

Leptin Treatment Reduces Body Weight and Corrects Blood Glucose Homeostasis in the ob/ob Mouse Having witnessed the behavior of individual islets in response to food over-consumption and insulin resistance, we next questioned if this growth could be refrained or even reversed by treating the ob/ob mice with leptin. Mice were injected intraperitoneally every day between 3 and 4 months of age. The physiological effects of this treatment were monitored regularly using different parameters. Parallel to their visibly reduced appetite we measured a decrease in body weight, blood glucose and insulin concentrations during treatment (FIG. 3A). However, this beneficial effect of leptin was not permanent as body weight rapidly increased after the end of the treatment period, to reach a mass similar to age-matched untreated ob/ob mice about one month later (see FIG. 1B for comparison). The treatment also had a beneficial impact on insulin sensitivity. At the end of the treatment period, intraperitoneal glucose tolerance tests on ob/ob mice demonstrated glucose excursions similar to those obtained from age-matched control mice (FIG. 3B).

Figure 4:
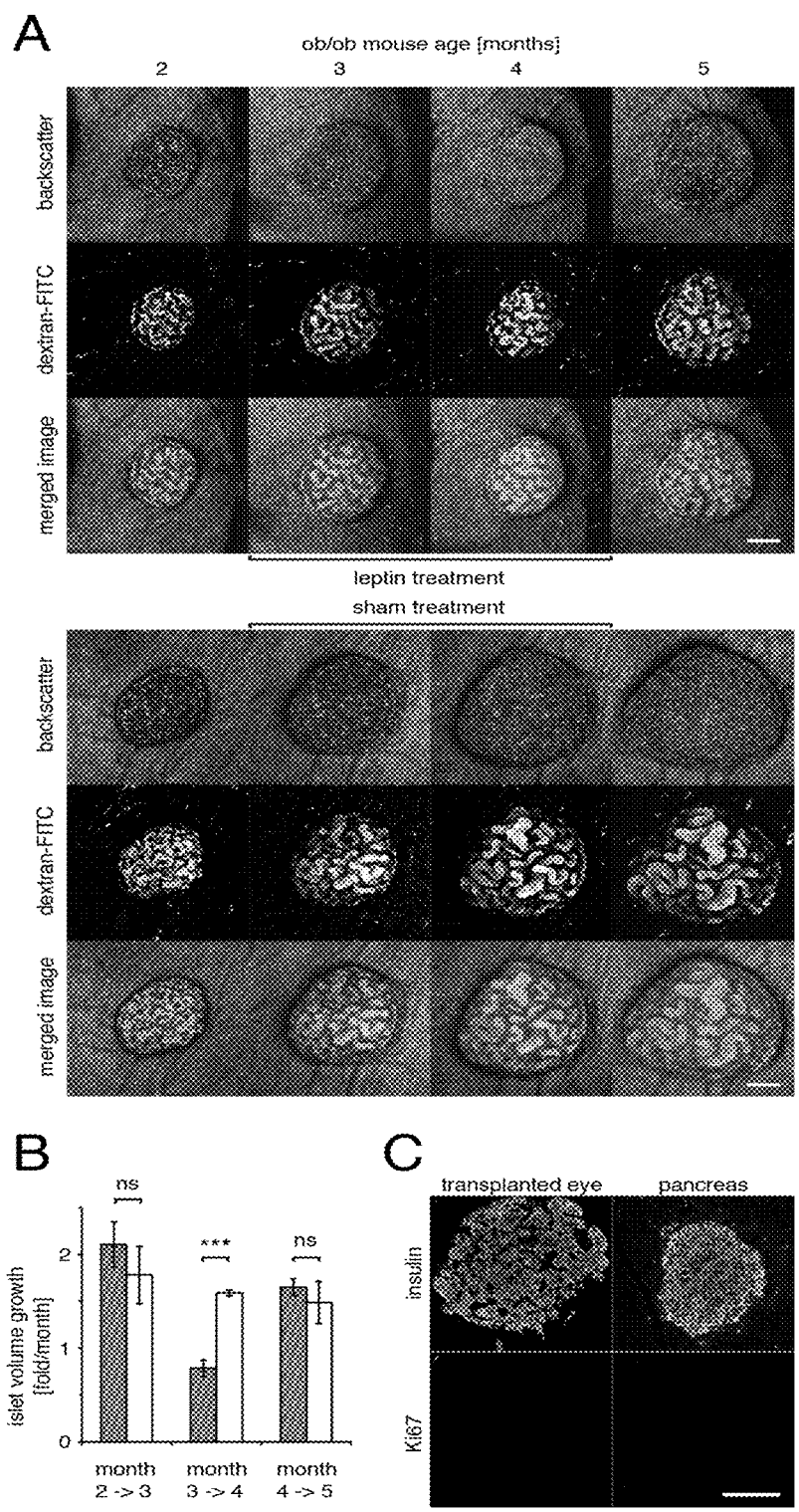
FIG. 4. Leptin treatment reverses dysregulation of ob/ob islets.(A) longitudinal in vivo imaging of islet grafts in ob/ob mice receiving leptin treatment (top) or sham treatment (bottom) between 3 and 4 months of age. Vasculature was visualized by tail-vein injection of dextran-FITC; (B) Islet volume analysis shows a reversal of islet growth during leptin treatment (gray bars) as compared to sham treatment (white bars); there was no difference in islet growth after the end of leptin or sham treatment. (C) immunohistochemistry on transplanted eye and pancreas samples from ob/ob mice at the end of the leptin treatment demonstrated the attenuated beta-cell proliferation by immunostaining for insulin and Ki67 (see FIG. 2F for comparison). Confocal images are representatives and shown as MIPs. Size bars=100 µm. Values are average±s.e.m.; ***p<0.001.
Figure 5:
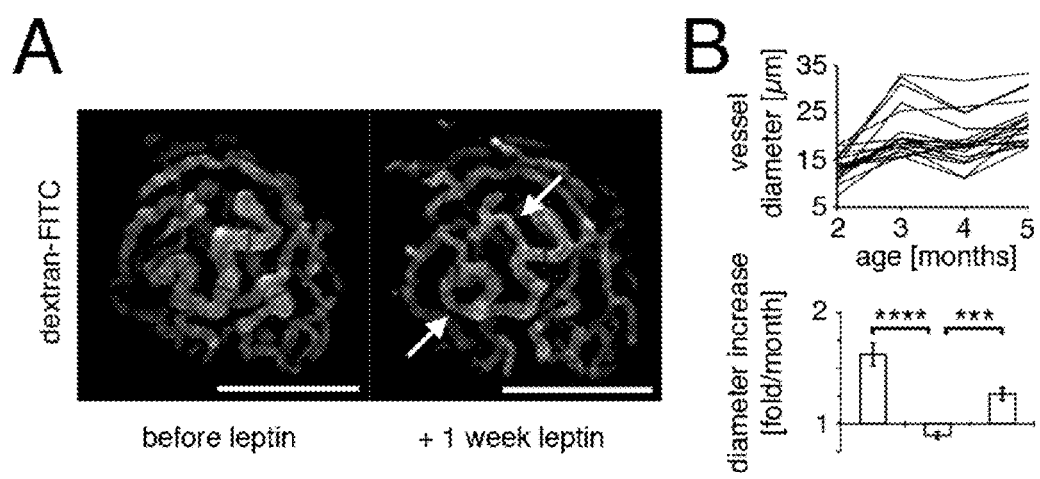
FIG. 5. Effect of leptin treatment on intra-islet vascularization. Islets were transplanted into the anterior chamber of the eye of ob/ob mice at the age of 4 weeks. At 3 months of age the mice received daily intraperitoneal injections of leptin. (A) leptin administration had a rapid effect on blood vessel diameters, as seen by in vivo imaging of the same islet before the beginning of the treatment, and after 1 week of treatment (vasculature was visualized by tail-vein injection of dextran-FITC). The same vessel segments could be identified at different time points and their diameter measured (see red lines). Note that we could observe angiogenesis following leptin administration (arrows); (B) longitudinal analysis of individual vessel diameters shows vessel morphological changes before, during and after leptin treatment (top traces, 20 vessel segments from islet grafts in ob/ob mouse are represented over time, lower bar graph shows corresponding average monthly diameter increases). Confocal images are representatives and shown as MIPs. Size bars=100 µm. Values are average±s.e.m.; *p<0.001; **p<0.0001.

Longitudinal In Vivo Imaging Reveals the Reversed Dysregulation of ob/ob Mouse Islets by Leptin The leptin treatment also exerts an influence on islet growth. Whereas sham-treated mice displayed a continuous adaptive growth of islet transplants, this growth was abolished and partially reversed under leptin-treatment (FIGS. 4A, B), in accordance with earlier reports (19, 20). At the end of the treatment the proliferation of beta cells was virtually abolished in both the engrafted islets and the in situ pancreatic islets from leptin-treated ob/ob mice (FIG. 4C). Following leptin treatment the average beta cell size reverted and showed no significant difference compared to age-matched untreated control mice, independently of whether the islets were transplanted or endogenously present in the pancreas (data not shown). The decrease in islet size could be explained in part by this decrease in individual beta cell size, as previously reported (21) and by morphological changes in intra-islet vasculature (FIG. 5). We measured a decrease in vessel diameter in islet grafts that was parallel to the lowered blood glucose levels. Interestingly, we could observe angiogenesis in the islet grafts at an early stage after leptin treatment, a biological phenomenon known to enhance blood perfusion and to be positively influenced by leptin via a synergistic stimulation with the angiogenic factors FGF-2 and VEGF (22).

Because of the restored leptin-driven adipo-insular feedback loop and the decrease in blood glucose levels we could observe the resulting regranulation of islet cells in vivo in transplanted islets by their stronger reflective optical properties (FIG. 4A), in accordance with the increased immunostaining for insulin perceived in islets from leptin-treated ob/ob mice (19). The normalization of insulin release in vivo after leptin treatment in the ob/ob mouse has been shown to be the result of mechanisms both dependent and independent on food intake (20).

Discussion

To test our novel concept of "reporter islets" reporting on the status of the in situ endocrine pancreas, we took the advantage of the fact that there is a significant remodeling capacity of the endocrine pancreas in the leptin-deficient ob/ob mouse. "Reporter islets" from the ob/ob mouse model were thus transplanted into the anterior chamber of the eye of a similar type of mouse for the investigation of islet cell mass regulation, representative of that going on in the endocrine pancreas. The "reporter islets" displayed obesity-induced growth and vascularization patterns that were identical to those observed in situ in the pancreas. These obesity-induced growth and vascularization patterns were reversed by leptin treatment both in the anterior chamber of the eye and in the in situ pancreas, showing evidence for a highly effective islet remodeling by the expansion or reduction of its insulin secretory potential. Such a remodeling capacity has so far only been indirectly suggested by cross-sectional studies or by the analysis of pancreatic islet populations at relatively low resolution in vitro. Hence, "reporter islets" can successfully reveal the molecular mechanisms regulating adaptive plasticity of the endocrine pancreas in vivo.

A number of different experimental approaches allow for the quantification of beta cell mass and for eventually displaying the remodeling of islets. In vitro techniques include the analysis of histological sections of pancreas by point counting morphometry (18) and the direct measurements of islet dimensions in dissected pancreatic tissue (23, 24). Ex vivo imaging techniques comprise the imaging of exteriorized pancreas by confocal microscopy (25) or optical coherence microscopy (26). Finally, several noninvasive in vivo imaging techniques aim at the longitudinal quantification of total beta cell mass, i.e. magnetic resonance imaging (MRI (27)), positron emission tomography (PET (28)), bioluminescence imaging (29), or combined multimodal imaging (30). None of these techniques offer the possibility to follow morphological changes in individual islets over time.

We now show that a few "reporter islets" can reveal, in a representative way, the remodeling of the in situ pancreatic islet population, expanding or reducing their insulin-secretory potential. Hence, this technique permits to "merge" the study of individual islets with the study of islet populations, and has the potential to replace multiple cross-sectional experiments with longitudinal studies. We thus propose in vivo imaging of "reporter islets" transplanted into the anterior chamber of the eye as a versatile tool to clarify molecular mechanisms as well as identify pharmacological compounds in the regulation of beta cell function and survival. Importantly, in humans a homologous use of "reporter islets", to both diagnose islet malfunction and monitor effects of specific individually based treatment regimens, may be envisaged as a novel personalized medicine approach. Our concept of "reporter islets" can be further developed by implementation of multiple high temporal cellular biomarkers for function and proliferation and also extended to other organs, with the ambition of identifying and understanding in detail molecular interactions and adaptive mechanisms at the cell and organ level, having implications for both physiology and pathology.

Methods Summary

Transgenic Mice Models

The ob/ob mice used for our experiments originate from Umeå, Sweden, and are inbred in our animal core facilities at the Karolinska Hospital. All experiments were performed according to Karolinska Institutet's guidelines for the care and use of animals in research and approved by the local animal ethics committees at Karolinska Institutet.

Transplantation of Pancreatic Islets into the Anterior Chamber of the Eye

Islets were isolated from female donor mice and transplanted into the anterior chamber of the eye of male recipients. We anesthetized mice using isoflurane (Baxter), and approximately 10-20 islets were transplanted into the anterior chamber of the mouse eye. Islets used for transplantation were selected to be of similar size for each experiment, independent of the mouse genotype. The mice were injected subcutaneously with Temgesic (Schering-Plough) for post-operative analgesia.

In Vivo Imaging of Intraocular Islet Grafts

Islet grafts in mice were imaged in vivo at specific time points after transplantation. We used an upright laser scanning confocal microscope based on TCS-SP2-AOBS (Leica) with a long-distance water-dipping objective (Leica HXC-APO 10x/0.30NA), and a custom-built stereotaxic head holder allowing to position the mouse eye containing the engrafted islets towards the objective. Viscotears (Novartis) was used as immersion liquid between the eye and the objective, and isoflurane was used to anesthetize the mice during in vivo imaging. Imaging of islet morphology was done by laser illumination at 633 nm, and collection of backscattered light at the same wavelength.

Leptin Treatment

Leptin treatment was performed by daily intraperitoneal injections of 1.5 µg/g body weight of recombinant human leptin (Amylin Pharmaceuticals), and sham treatment was performed by intraperitoneal injection of water instead of leptin.

References

1. Butler P C, Meier J J, Butler A E, Bhushan A (2007) The replication of beta cells in normal physiology, in disease and for therapy. *Nat Clin Pract Endocrinol Metab* 3:758-768.
2. Speier S et al. (2008) Noninvasive in vivo imaging of pancreatic islet cell biology. *Nat Med* 14:574-578.
3. Speier S et al. (2008) Noninvasive high-resolution in vivo imaging of cell biology in the anterior chamber of the mouse eye. *Nature Protocols* 3:1278-1286.
4. Ingalls A M, Dickie M M, Snell G D (1950) Obese, a new mutation in the house mouse. *J Hered.* 41:317-318.
5. Westman S (1968) Development of the obese-hyperglycaemic syndrome in mice. *Diabetologia* 4:141-149.
6. Lindstrom P (2007) The physiology of obese-hyperglycemic mice [ob/ob mice]. *Scientific-WorldJournal* 7:666-685.
7. Zhang Y et al. (1994) Positional cloning of the mouse obese gene and its human homologue. *Nature* 372:425-432.
8. Seufert J, Kieffer T J, Habener J F (1999) Leptin inhibits insulin gene transcription and reverses hyperinsulinemia in leptin-deficient ob/ob mice. *Proc Natl Acad Sci USA* 96:674-679.
9. Seufert J (2004) Leptin effects on pancreatic beta-cell gene expression and function. *Diabetes* 53 Suppl 1:S152-8.
10. Wrenshall G A, Andrus S B, Mayer J, JONES A K, DOLAN P (1955) High levels of pancreatic insulin coexistent with hyperplasia and degranulation of beta cells in mice with the hereditary obese-hyperglycemic syndrome. *Endocrinology* 56:335-340.
11. Kim A et al. (2009) Islet architecture: A comparative study. *Islets* 1:129-136.
12. Adeghate E, Donath T (1990) Morphological findings in long-term pancreatic tissue transplants in the anterior eye chamber of rats. *Pancreas* 5:298-305.
13. Hellerström C, Hellman B (1961) The blood circulation in the islets of Langerhans visualized by the fluorescent dye vasoflavine. Studies in normal and obese-hyperglycemic mice. *Acta Soc Med Ups* 66:88-94.
14. Starich G H, Zafirova M, Jablenska R, Petkov P, Lardinois C K (1991) A morphological and immunohistochemical investigation of endocrine pancreata from obese ob+/ob+ mice. *Acta Histochem* 90:93-101.
15. Menger M D, Vajkoczy P, Leiderer R, Jäger S, Messmer K (1992) Influence of experimental hyperglycemia on microvascular blood perfusion of pancreatic islet isografts. *J Clin Invest* 90:1361-1369.
16. Morioka T et al. (2007) Disruption of leptin receptor expression in the pancreas directly affects beta cell growth and function in mice. *J Clin Invest* 117:2860-2868.
17. Tassava T, Okuda T, Romsos D (1992) Insulin secretion from ob/ob mouse pancreatic islets: effects of neurotransmitters. *Am J Physiol* 262:E338-43.
18. Bock T., Pakkenberg B., Buschard K. (2003) Increased islet volume but unchanged islet number in ob/ob mice. *Diabetes* 52:1716-1722.
19. Khan A et al. (2001) Long-term leptin treatment of ob/ob mice improves glucose-induced insulin secretion. *Int J Obes Relat Metab Disord* 25:816-821.
20. Lee J-W, Romsos D R (2003) Leptin administration normalizes insulin secretion from islets of Lep(ob)/Lep (ob) mice by food intake-dependent and -independent mechanisms. *Exp Biol Med (Maywood)* 228:183-187.
21. Park S, Hong S M, Sung S R, Jung H K (2008) Long-term effects of central leptin and resistin on body weight, insulin resistance, and beta-cell function and mass by the modulation of hypothalamic leptin and insulin signaling. *Endocrinology* 149:445-454.
22. Cao R, Brakenhielm E, Wahlestedt C, Thyberg J, Cao Y (2001) Leptin induces vascular permeability and synergistically stimulates angiogenesis with FGF-2 and VEGF. *Proc Natl Acad Sci USA* 98:6390-6395.
23. Parsons J A, Bartke A, Sorenson R L (1995) Number and size of islets of Langerhans in pregnant, human growth hormone-expressing transgenic, and pituitary dwarf mice: effect of lactogenic hormones. *Endocrinology* 136:2013-2021.
24. Alanentalo T et al. (2008) High-resolution three-dimensional imaging of islet-infiltrate interactions based on optical projection tomography assessments of the intact adult mouse pancreas. *J Biomed Opt* 13:054070.
25. Nyman L, Ford E, Powers A, Piston D (2010) Glucose-dependent blood flow dynamics in murine pancreatic islets in vivo. *Am J Physiol Endocrinol Metab* 298:E807-14.
26. Villiger M et al. (2009) In vivo imaging of murine endocrine islets of Langerhans with extended-focus optical coherence microscopy. *Diabetologia* 52:1599-1607.
27. Lamprianou S et al. (2011) High-resolution magnetic resonance imaging quantitatively detects individual pancreatic islets. *Diabetes* 60:2853-2860.
28. Singhal T et al. (2011) Pancreatic beta cell mass PET imaging and quantification with [11C]DTBZ and [18F] FP-(+)-DTBZ in rodent models of diabetes. *Mol Imaging Biol* 13:973-984.
29. Park S-Y, Bell G I (2009) Noninvasive monitoring of changes in pancreatic beta-cell mass by bioluminescent imaging in MIP-luc transgenic mice. *Horm Metab Res* 41:1-4.
30. Virostko J et al. (2011) Multimodal image coregistration and inducible selective cell ablation to evaluate imaging ligands. *Proceedings of the National Academy of Sciences* 108:20719-20724.
31. Ellett J, Evans Z, Zhang G, Chavin K, Spyropoulos D (2009) A rapid PCR-based method for the identification of ob mutant mice. *Obesity (Silver Spring)* 17:402-404.

Materials and Methods

Mouse Model

The ob/ob mice used for our experiments originate from Umeå, Sweden, and are inbred in our animal core facilities at the Karolinska Hospital. The discrimination from control lean littermates was achieved by phenotypic and genotypic analysis (31). All experiments were performed according to Karolinska Institutet's guidelines for the care and use of animals in research and approved by the local animal ethics committees at Karolinska Institutet.

Physiological Measurements and Leptin Treatment

Body weight and blood glucose levels were measured in a minimum of 7 mice. Glucose concentrations were obtained using Accu-Chek™ Aviva monitoring system (Roche). Glucose tolerance tests were performed by intraperitoneal injection of 2 mg glucose per gram body weight in mice fasted for 16 hours (n≥5). Plasma insulin concentrations from a minimum of 3 mice per condition were measured using mouse insulin ELISA plates (Mercodia). Leptin treatment was performed by daily intraperitoneal injections of 1.5 µg/g body weight of recombinant human leptin (Amylin Pharmaceuticals), and sham treatment was performed by intraperitoneal injection of water instead of leptin.

Transplantation of Pancreatic Islets into the Anterior Chamber of the Eye

Islets were isolated from female donor mice and transplanted into the anterior chamber of the eye of male recipients, using a previously described technique (2). We anesthetized mice using isoflurane (Baxter), and approximately 10-20 islets were transplanted into the anterior chamber of the mouse eye. Islets used for transplantation were selected to be of similar size for each experiment, independent of the mouse genotype. The mice were injected subcutaneously with Temgesic™ (Schering-Plough) for postoperative analgesia.

In Vivo Imaging of Intraocular Islet Grafts

Islet grafts in mice were imaged in vivo at specific time points after transplantation as previously described (2). We used an upright laser scanning confocal microscope based on TCS-SP2-AOBS (Leica) with a long-distance waterdipping objective (Leica HXC-APO 10×/0.30NA), and a custom-built stereotaxic head holder allowing to position the mouse eye containing the engrafted islets towards the objective. Viscotears™ (Novartis) was used as immersion liquid between the eye and the objective, and isoflurane was used to anesthetize the mice during in vivo imaging. Imaging of islet morphology was done by laser illumination at 633 nm, and collection of backscattered light at the same wavelength. For visualization of blood vessels we injected 100 µl of a solution containing 2.5 mg/ml of 500 kDa FITC-labeled dextran (Invitrogen) into the tail vein, and imaged fluorescence using 496 nm excitation wavelength. Scanning speed and laser intensities were adjusted to avoid any cellular damage to the mouse eye or islet graft.

Tissue Sections and Immunohistochemistry

Dissected tissues were briefly rinsed with PBS, fixed for 48 h at room temperature using formalin, and dehydrated and embedded in paraffin. Five-micron thick sections mounted on precoated microscope slides were dewaxed by xylene and progressively rehydrated before processing. Insulin was stained using chicken anti-insulin (1:200 dilution, Abcam) followed by goat anti-chicken Alexa™ 488 (1:1000 dilution, Invitrogen) antibodies; blood vessels were stained using rat anti-mouse CD31 (1:50 dilution, BD Pharmingen), followed by incubation of biotinylated goat anti-rat (5 µg/ml, Vector Labs) and amplification with HRP-streptavidin/Alexa™ 647-tyramide (Invitrogen); proliferation was assessed by using mouse anti-human Ki67 (1:50 dilution, Novocastra) together with M.O.M. biotinylated anti-mouse IgG (Vector Labs), and amplified using HRP-streptavidin/Alexa 647-tyramide. Nuclei were stained and slides were preserved by cover glass mounting using ProLong™ Gold Antifade Reagent with DAPI (Invitrogen). Slides were imaged using a BD Pathway 855 system (BD Biosciences). Insulin, CD31, Ki67 and DAPI stainings were imaged using a 20×/0.75NA UApo/340 Olympus objective, and overviews of pancreatic sections stained by hematoxylin/eosin were obtained by montage capture mode using a 4×/0.16NA UPlan SApo Olympus objective.

Image Processing and Analysis

AutoQuant X2 (Media Cybernetics) was used for blind deconvolution of all in vivo confocal images before image analysis. Islet volume was analyzed based on the backscatter signal channel, using Matlab™ and the Image Processing Toolbox (Mathworks). The islet "equatorial volume", i.e. the volume from the top of the islet down to the calculated equator, was used to represent the volume and calculate islet growth. We analyzed a minimum of 3 islet grafts per animal to determine islet growth, with a minimum of 3 mice per category. Individual vessel segments were identified at different imaging time points and their diameter measured using Volocity™ (Perkin Elmer). We established image analysis protocols in Volocity™ for automated analysis of histological sections. The average beta cell section area was obtained by dividing the insulin-stained area by the total number of DAPI-stained nuclei enclosed in this area (minimum of 1000 cells per tissue). Beta cell proliferation rate was obtained by counting Ki67-positive nuclei and dividing by the total number of DAPI-stained nuclei in insulin-positive cells (minimum of 10000 cells per transplanted eye or pancreas). Volocity™ was used for image display and Photoshop CS5 (Adobe) for image assembly.

Statistical Analysis

All results are presented as average±SEM. Student's t test was used for determining statistical significance, and P values<0.05 were considered significant.

I claim:

1. A method for monitoring a physiological status of an in situ pancreas in a human subject during a course of treatment, comprising monitoring morphological changes over time in transplanted pancreatic islets of Langerhans transplanted on an eye of the human subject, wherein the morphological changes over time in the transplanted pancreatic islets tissue on the eye of the subject indicate a physiological status of the in situ pancreas in the human subject during a course of treatment.

2. The method of claim 1, wherein the method is used to monitor efficacy of a course of treatment for a disorder affecting the pancreas.

3. The method of claim 2, wherein the course of treatment comprises administration of a therapeutic to the subject, and wherein the method monitors efficacy of the therapeutic in the subject.

4. The method of claim 2, wherein the course of treatment comprises a diet and/or an exercise regimen, and wherein the method monitors efficacy of the diet and/or exercise regimen in the subject.

5. The method of claim 1, wherein the transplanted pancreatic islets are obtained from the subject.

6. The method of claim 1, wherein the morphological changes are selected from the group consisting of cell size in the pancreatic islets, cell volume in the pancreatic islets, cell area in the pancreatic islets, cell shape in the pancreatic islets, cell death in the pancreatic islets, cell proliferation in the pancreatic islets, cell mass in the pancreatic islets, blood perfusion in the pancreatic islets, optical reflectivity of cells in the pancreatic islets, and granulation of cells in the pancreatic islets.

7. The method of claim 1, wherein the morphological changes in the transplanted pancreatic islets are determined at two or more time points.

8. The method of claim 2, wherein the disorder is diabetes.

9. The method of claim 8, wherein the methods further comprise administering a therapeutic or test compound to the subject, and monitoring morphological changes resulting from the administering.

10. The method of claim 9, wherein the morphological changes in the transplanted pancreatic islets are determined at two or more time points after the administering.

11. The method of claim 1, wherein the morphological changes are monitored by microscopy.

12. The method of claim 1, wherein the pancreatic islets are transplanted into an anterior chamber of the eye of the subject.

13. The method of claim 1, wherein the pancreatic islets are transplanted onto an iris of the eye of the subject.

14. The method of claim 8, wherein the course of treatment comprises administration of a therapeutic to the subject, and wherein the method monitors efficacy of the therapeutic in the subject.

\* \* \* \* \*